United States Patent [19]

Ostrow et al.

[11] Patent Number: 5,344,384
[45] Date of Patent: Sep. 6, 1994

[54] MAGNETOTHERAPY APPARATUS

[75] Inventors: Alvin Ostrow; Grigory Grinshpon, both of Englewood, N.J.

[73] Assignee: Electromagnetic Bracing Systems, Inc., Boca Raton, Fla.

[21] Appl. No.: 989,336

[22] Filed: Dec. 11, 1992

[51] Int. Cl.⁵ ............................................. A61N 1/00
[52] U.S. Cl. ...................................................... 600/13
[58] Field of Search ....................................... 600/9–15; 604/20; 607/48–52

[56] References Cited

U.S. PATENT DOCUMENTS

| | | | |
|---|---|---|---|
| 4,574,809 | 3/1986 | Talish et al. | 128/419 F |
| 4,616,629 | 10/1986 | Moore | 128/1.5 |
| 4,757,804 | 7/1988 | Griffith et al. | 128/1.5 |
| 4,993,413 | 2/1991 | McLeod et al. | 128/419 F |
| 5,000,178 | 3/1991 | Griffith | 128/419 F |
| 5,014,699 | 5/1991 | Pollack et al. | 128/419 F |
| 5,038,797 | 8/1991 | Batters | 128/798 |
| 5,100,373 | 3/1992 | Liboff et al. | 600/13 |
| 5,131,904 | 7/1992 | Markoll | 600/14 |

FOREIGN PATENT DOCUMENTS 8501881   5/1985   World Int. Prop. O. ............. 600/15

*Primary Examiner*—Lee S. Cohen
*Assistant Examiner*—J. P. Lacyk
*Attorney, Agent, or Firm*—Natter & Natter

[57] ABSTRACT

A magnetotherapy apparatus includes an applicator wrap segmented into a grid of hinged panels. The wrap is adapted to be placed around an injured body member to provide a brace or preform for a conventional cast. Each of the panels further includes a magnetic coil for generating an electromagnetic field directionally oriented perpendicular to a target area. The magnetic fields generated in the adjacent panels are of opposite polarity and cumulatively interact for deeper magnetic flux penetration. An electrostimulation component includes stimulator pads which are selectively energized to provide muscle and/or transcutaneous nerve stimulation for pain sedation. Alternatively, the stimulator pads are used for an electrophoretic pharmaceutical delivery system wherein electrically charged porous pads are in fluid communication with a drug medium.

9 Claims, 4 Drawing Sheets

FIG. 2
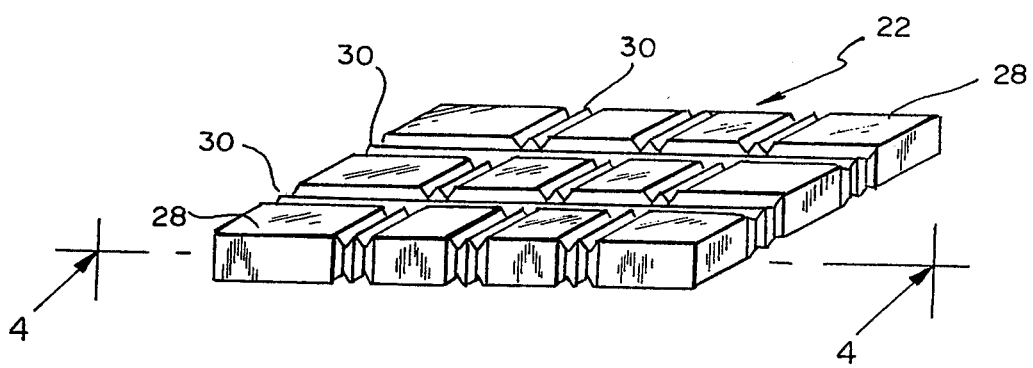
FIG. 3
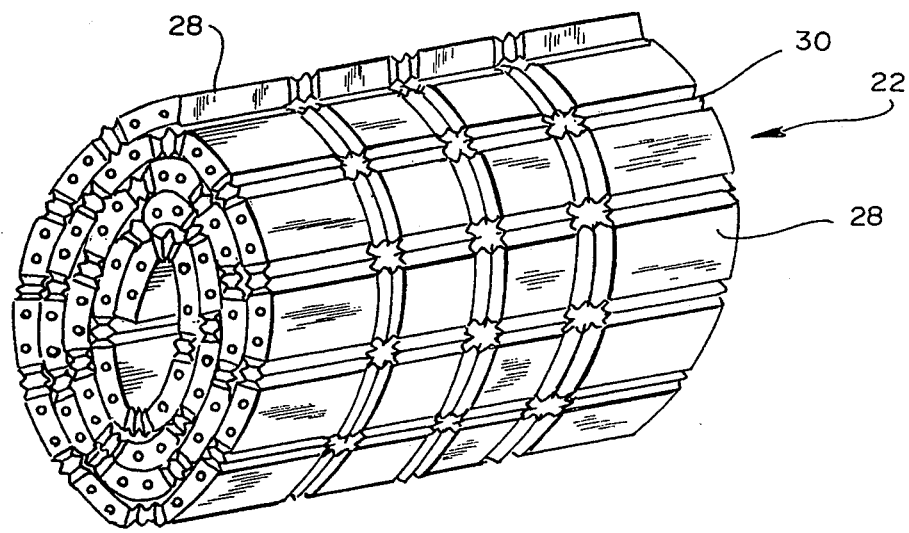
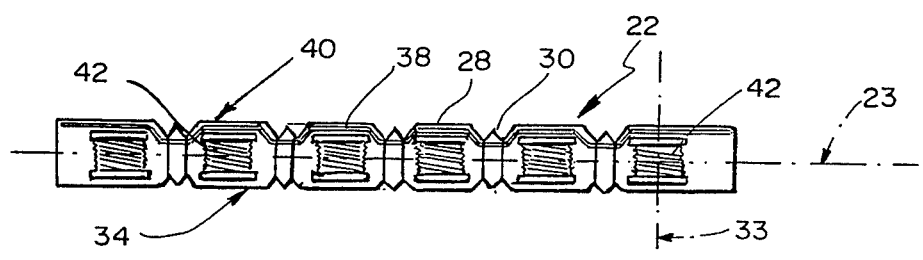
FIG. 4

5,344,384

MAGNETOTHERAPY APPARATUS

FIELD OF THE INVENTION

This invention relates generally to medical appliances and especially to the application of electrical energy for therapeutic body treatment.

In particular, the device of this invention concerns a magnetotherapy apparatus incorporated within an orthotic brace or preform for a conventional cast. Ancillary treatment modalities are provided by an optional neuromuscular electrostimulation component and by an electrophoretic pharmaceutical delivery system.

BACKGROUND ART

The use of electrical and electromagnetic therapy for stimulating growth and repair of living tissue has been known and recognized as an acceptable form of treatment. Prior devices, utilizing non-invasive magnetic fields, lacked the ability to simultaneously brace and treat a fracture site. Furthermore, the previously known devices did not provide the availability of multiple treatment protocols.

The electromagnetic apparatus disclosed in U.S. Pat. No. 5,014,699, for example, placed a transducer over a previously formed plaster cast. Similarly, the multi-conductor ribbon cable treatment shown in U.S. Pat. No. 4,993,413 and the flat bands described in U.S. Pat. No. 4,757,804, did not provide an orthotic support. Furthermore, the magnetic fields generated by the aforementioned apparatus were not directionally oriented perpendicularly with respect to a target area. Although the apparatus shown in U.S. Pat. No. 5,100,373 generates normally directed magnetic fields from two treatment heads, the heads are not positioned for advantageously combining magnetic flux as in the present invention.

U.S. Pat. No. 4,616,629 shows a magnetic coil embedded in an orthopedic cast and U.S. Pat. No. 4,574,809 describes another form of cast-embedable coil for electromagnetic therapy. These last two mentioned patents utilize a conventional cast with a removable plug-in connection for a pulse-signal generator. Although these devices provide electromagnetic therapy in combination with a bracing system, the instant device can be used with or without a plaster or fiberglass cast and is furthermore portable for providing continuous treatment, if required.

BRIEF SUMMARY OF THE INVENTION

The magnetotherapy apparatus of this invention encompasses an applicator wrap for applying electromagnetic radiation to a mammalian host for therapy. The applicator wrap is externally self-supported contiguous to a body surface to provide a brace or preform.

The wrap is formed of molded plastic material provided with integral hinges for flexibility and is adapted to surround and firmly brace an injured body member. In addition, a conventional cast can be applied over the wrap if additional support or immobilization of the member is required.

The wrap is provided with a network of electrically conductive coils providing a "checkerboard" pattern of magnetic fields that are cumulatively interactive.

A feature of this invention is that the electromagnetic therapy provides deep magnetic flux penetration within a target area.

Another aspect of this invention concerns the application of electrical energy for nerve stimulation, for pain sedation, for the prevention of atrophy and for the acceleration of bone healing.

Another feature of this invention is the ability to provide auxiliary treatment to areas of the human body otherwise unaccessible when encased within a conventional brace or cast.

In addition, a fluid medium delivery component can be optionally utilized for medicating the target area.

It should be apparent that the multi-modal nature of this apparatus covers a broad spectrum of treatment protocols including injuries to soft tissue and hard tissue structures that may be applied at selected locations on the human body.

In view of the foregoing, it should be apparent that the present invention overcomes many of the shortcomings and disadvantages of the prior art and provides an improved magnetic therapy apparatus.

Having thus summarized the invention, it will be seen that it is an object thereof to provide a magnetotherapy apparatus of the general character described herein which is not subject to the aforementioned deficiencies.

Another object of this invention is to provide a magnetotherapy apparatus providing an integral brace or preform.

A further object of this invention is to provide a magnetotherapy device having selective curative regimens that can be applied severally or jointly.

A still further object of this invention is to provide a magnetotherapy apparatus that can be comfortably worn by the patient, that is light in weight, that is portable in use and that is cost effective to manufacture.

Other objects of this invention in part will be apparent and in part will be pointed out hereinafter.

With these ends in view, the invention finds embodiment in certain combinations of elements and arrangements of parts by which the aforementioned objects and certain other objects are hereinafter attained, all as more fully described with reference to the accompanying drawings and the scope of which is more particularly pointed out and indicated in the appended claims.

BRIEF DESCRIPTION OF THE DRAWING

In the accompanying drawings, in which is shown an exemplary embodiment of the invention:

FIG. 2 is a perspective view of a portion of an applicator wrap used in conjunction with the apparatus of this invention illustrating a grid of hinged panels;

FIG. 3 is a perspective view showing the applicator wrap in a stored configuration prior to being used;

FIG. 4 is a sectional view taken substantially along line 4—4 of FIG. 2 illustrating the placement of a series of magnetic coils within the applicator wrap;

DETAILED DESCRIPTION OF THE INVENTION

With specific reference now to the figures in detail, it is stressed that the particulars shown are by way of example and for the purpose of illustrative discussion of the preferred embodiment of the present invention only and are presented in the cause of providing what is believed to be the most useful and relatively understood description of the principals and conceptual aspects of the invention. In this regard, no attempt is made to show structural aspects of the invention in more detail than is necessary for a fundamental understanding of the invention, the description taken with the drawings making it apparent to those skilled in the art how the several forms of the invention may be embodied in practice.

Figure 1:
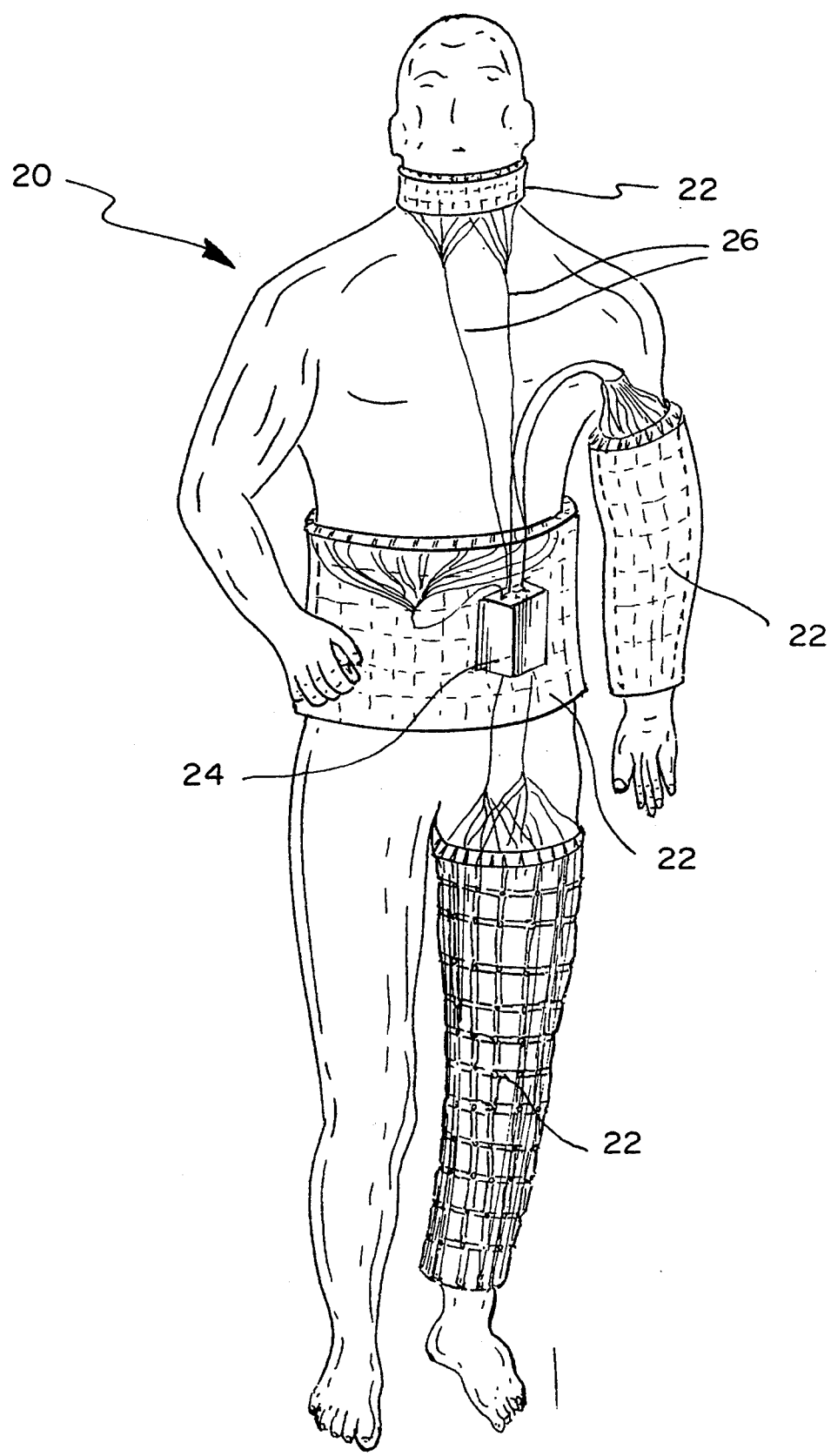
FIG. 1 is a front elevational view pictorially illustrating a magnetotherapy apparatus of this invention as applied to selected portions of the human body including the neck, arm, lower back and leg.

Referring now to FIG. 1, there is illustrated a pictorial representation of a magnetotherapy apparatus 20 in accordance with this invention. The magnetotherapy apparatus 20 is typically shown at selected anatomical locations on a human body.

The apparatus 20 is comprised of an applicator wrap 22, a portable operating console 24 that incorporates a power supply source and a cable harness 26 for conductively coupling the console 24 to the applicator wrap 22.

The applicator wrap 22, as best shown in FIGS. 2 and 3, is fabricated from a thermoplastic material and preferably molded with a grid-like pattern having linked panels 28 connected by integral flexible hinges 30. A Velcro closure is utilized for securing the wrap 22 against afflicted areas on the patient's body as for example as shown in FIG. 1. The panels 28 provide the required firmness for use in orthotic bracing and the hinges 30 provides compliancy for conforming the wrap 22 to the treatment site. It should of course, be apparent that the wrap 22 can be manufactured in different lengths, shapes and sizes as necessary for selected applications.

Figure 5:
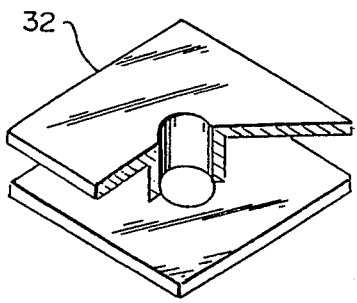
FIG. 5 is an isolated enlarged perspective view, partially in section, showing a hollow core used in the fabrication of the magnetic coil.

A plurality of hollow cores 32, which are made of ferrite or an equivalent conductive alloy, are positioned within each of the panels 28 such that a longitudinal axis 33 of the core 32 is perpendicular to a transverse axis 23 of the wrap 22. A contact surface 34 of the wrap 22 is intended for placement contiguous to the patient's skin. By way of example, the cores 32, such as shown in FIG. 5, have a square base approximately ⅜ in. on each side and are spaced approximately ⅜ in. center-to-center to provide about four (4) cores 32, per square in. within the wrap 22. Furthermore, the cores 32 can be imbedded in the thermoplastic material during the molding process and thus secured in place by the surrounding thermoplastic material. Alternatively, the cores 32 can be glued in place using, for example, conductive epoxy cement. It should be observed however, that before the cores 32 are fixed in position, a conductive wire 36 is preferably closely wound evenly around each of the cores 32 to provide a treatment coil 42 for generating magnetic fields as will be further discussed hereinafter.

Further in connection with the fabrication of the wrap 22, the preferred embodiment illustrated herein also includes electromagnetic radiation shielding in the form of a metalized material forming a substrate 38 comprised of a layer of narrow gauge metal wire or mesh in%bedded within the thermoplastic material. The electromagnetic radiation shielding substrate 38 is positioned adjacent an outer surface 40 of the wrap 22. The substrate 38 prevents "leakage" of the electromagnetic field and creates a rebound affect to contain and increase the effectiveness of the magnetic field.

Figure 6:
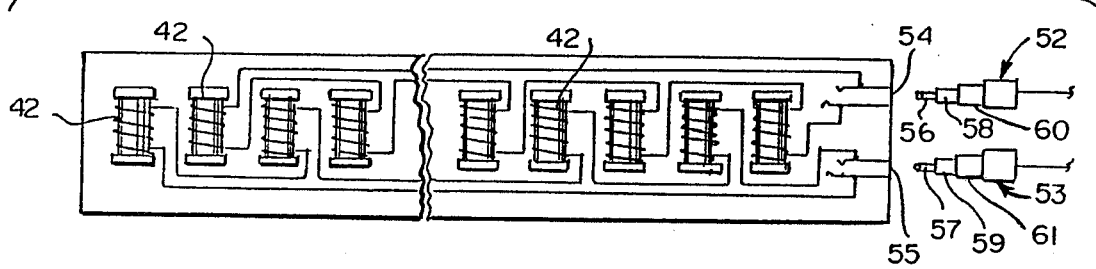
FIG. 6 is an elevational view, to enlarge scale, of a portion of the applicator wrap showing the hollow core with helical conductive windings and the electrical circuitry for energizing the magnetic coils.
Figure 7:
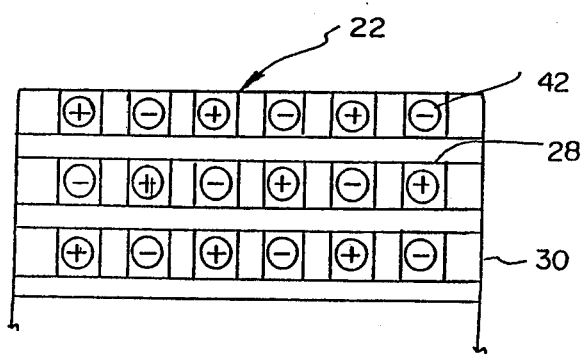
FIG. 7 is a plan view of the applicator wrap illustrating diagrammatically the "checkerboard" pattern of the magnetic coils and their corresponding polarities.

Referring once again to the coils 42, it will be noted in FIG. 6 that the wiring sequence around each core 42 provides for a current flow through adjacent magnetic coils 42 in opposite directions to thereby generate a "checkboard" of magnetic fields of alternate polarities as graphically depicted in FIG. 7. This is accomplished by conductively coupling the windings of coils 42 in two circuits as will be further described hereinafter.

Figure 8:
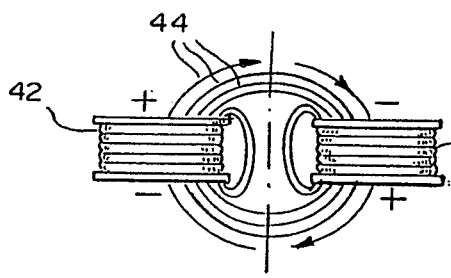
FIG. 8 is an elevational view showing the combined lines of induction radiating from adjacent magnetic coils of opposite polarity.
Figure 9:
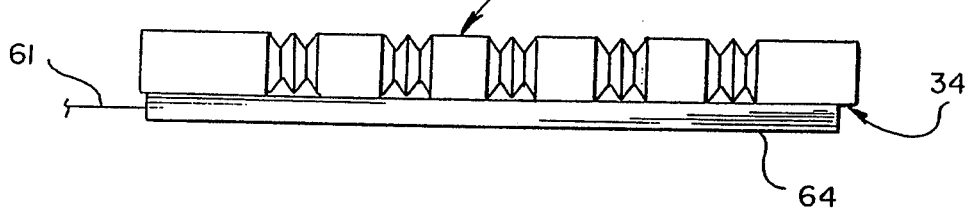
FIG. 9 is an elevational view illustrating the applicator wrap of this invention in conjunction with an electrostimulation component.
Figure 10:
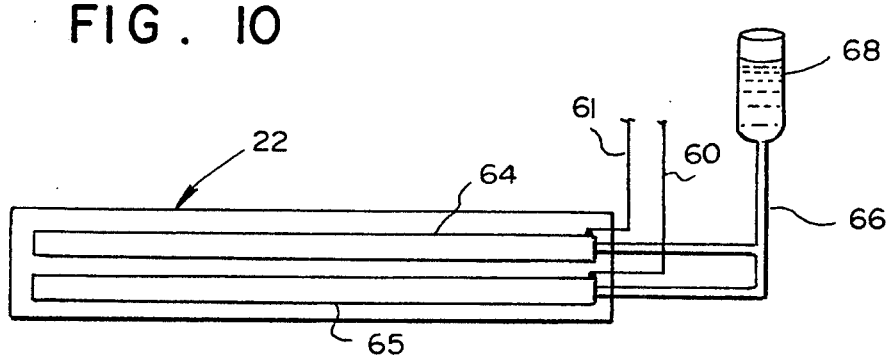
FIG. 10 is a plan view of an electrophoretic pharmaceutical delivery system for use with the apparatus of this invention.

In the isolated sectional view of FIG. 8 two adjacent coils 42 have magnetic lines of induction 44. The direction of the induction vector is indicated by the arrow heads on each of the lines of induction 44. It will thereby be observed that the cooperative interaction of the magnetic fields generated by adjacently placed coils 42 are combined, in contrast to the interaction of magnetic fields of similar polarity, to provide a greater magnitude of magnetic flux and concurrently a deeper local penetration into muscle and bone tissue.

Figure 11:
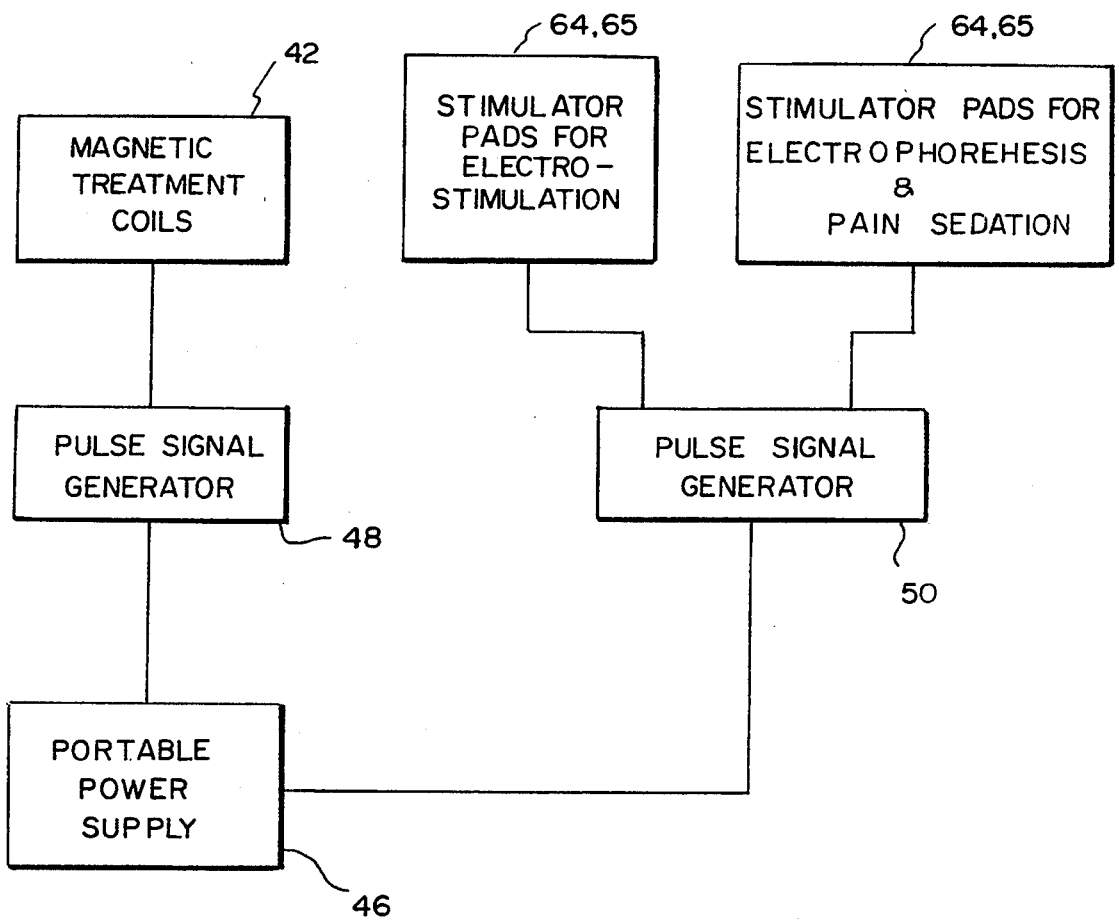
FIG. 11 is a block diagram of the apparatus of this invention showing a circuit divided into convenient functional sections.

The preferred power supply is an electrochemical cell such as a commercially available nickel cadmium 9 volt rechargeable battery. The battery is housed within the console 24. With reference to FIG. 11 it will seen that two independent pulse generators 48, 50 are included within the console 24. The generator 48 supplies a.c. power for the electromagnetic field therapy and the generator 50 supplies d.c. power for electrostimulation and electrophoretic pharmaceutical delivery system both of which will be described hereinafter.

With regard to the electromagnetic field therapy, a computerized chip distribution system monitors and supplies the strongest current directly to coils 42 positioned over the target area according to a treatment protocol. A weaker current will be supplied to the secondary anatomical structure surrounding the target area. This is an optional feature which is built into the console 24.

Referring once again to the pulse signal generator 48, an asymmetrical trapezoidal waveform having approximately a 15%–16% greater negative value than positive value is fed to the magnetic treatment coils 42. For this purpose the wire harness 26 is conductively coupled to the applicator wrap 22 by a set of (three-conductor) connector plugs 52, 53 that are accommodatingly received within a corresponding set of sockets 54, 55. Referring to FIG. 6 it will be seen that the set of plugs 52, 53 contain three conductors, 56, 58, 60 and 57, 59, 61, respectively. The conductors 56, 57 and 58, 59, when inserted within the respective sockets 54, 55 complete two independent circuits for energizing alternating treatment coils 42. It will be noted that when the current flows in a clockwise direction through the windings in the treatment coils 42 in one circuit defined by plug 52, the current will correspondingly flow in a counterclockwise direction through the windings of the treatment coils 42 within the other circuit defined by plug 53. The pulsed trapezoidal waveform has a periodic frequency within the range of 10–100 hertz and preferably about 16 hertz is used for the electromagnetic field therapy. The preferred range of magnetic flux density should not exceed 100 gauss.

The magnetotherapy apparatus 20 can best be utilized for inducing an electromagnetic field into the human body extradermally and can simultaneously brace and treat a fracture site. Furthermore a plaster or fiberglass cast can be placed over the apparatus 20 which then functions as a brace preform.

Further with regard to the additional treatment modalities, the electrostimulation component provides galvanic muscle strengthening by nerve stimulation for producing muscle contractions that deter the onset of atrophy in an immobilized body part. The electrostimulation regimen is also effective for reversing the degenerative affects of atrophia.

This aspect of the invention includes the incorporation of a set of conductive stimulator pads 64, 65. The stimulator pads 64, 65 are applied to the contact surface 34 of the wrap 22. The conductors 60, 61 provide the respective pads 64, 65 with opposite charges of d.c. current. When the wrap 22 is placed on the patient, the stimulator pads 64, 65 are in direct contact with the skin surface.

It should be noted that the pulse generator 50 provides a direct current of low frequency having a trapezoidal waveform pulsed at between 20–90 hertz. The pulsed timing sequence is set for approximately 50% "on" and about 50% "off" during each cycle. The treatment cycle has a duration of 6–15 seconds "on" and up to 40 seconds "off". It should be understood however that the pulse generator 50 can be modulated in accordance with the desired electrostimulation therapy.

The previously described muscular electrostimulation can be used independently or in combination with the electromagnetic field therapy.

Another aspect of this invention concerns the electrophoretic pharmaceutical delivery system. The purpose of the electrophoresis is to utilize an electrical field to influence the transfer and metabolism of the drug medium into the patient's body. For this purpose, the stimulator pads 64, 65 include a porous material that is connected by a network of tubing 66 supplied with a selected drug medium from a reservoir 68 through a gravity feed system. It should further be noted that the stimulator pads 64, 65 are thus electrically energized by the pulse generator 50 through the respective conductors 60, 61 and that each of the pads 64, 65 will at all times be oppositely charged. In operation the pads 64, 65 receive the pharmaceutical medium from the branch tubing 66. The fluid medium is distributed throughout the pads 64, 65 by capillary action. The application of the electrical current provides an ionization effect producing a more effective delivery path to the patient. This is particularly advantageous when a conventional cast has been placed over the magnetotherapy apparatus 20 and thus the afflicted area is otherwise inaccessible to direct drug therapy.

The signals utilized in connection with the electrophoretic system include d.c. current modulation having a trapezoid waveform with continuous pulses modulated at between 20 to 90 hertz. The pulses have a 10% to 20% "off" and 80% to 90% "on" timing for maximum effectiveness. It should be further observed that this treatment mode also provides, as an adjunct, trans- cutaneous nerve stimulation for pain sedation. In this regard, the transcutaneous nerve stimulation can be effected concurrently with or independently of the electrophoretic drug therapy.

It should thus be apparent that a clinician or patient can choose options of desired therapy singularly or in combination using the operating counsel 24.

It will be evident to those skilled in the art that the apparatus of this invention is not limited to the details of the forgoing illustrated embodiments and that the present may be embodied in other specific forms without departing from the spirit or essential attributes thereof.

The present embodiment is therefore to be considered in all respects as illustrative and not in a restrictive sense. The scope of the invention being indicated by the appended claims rather than by the forgoing description and all changes which come which come within the meaning and range of equivalency of the claims are therefore intended to be embraced therein.

Having thus described the invention, there is claimed as new and desired to be secured by Letters Patent:

1. A magnetotherapy apparatus comprising an applicator wrap, having an outer surface and an inner surface having a plurality of panels hingedly linked and adapted to surround and brace an injured body member adjacent said inner surface, a magnetic coil positioned within each of said panels for simultaneously generating an electromagnetic field in each of said panels, said magnetic coil including a core having a plurality of windings, said windings of each coil being conductively coupled to the windings of alternate successive coils to form at least two respective circuits, whereby current flow through the windings in one circuit is in a first direction and current flow through the windings in another circuit is in a second direction to provide magnetic fields of opposite polarity in the coils of the respective circuits when energized, wherein a longitudinal axis of the magnetic coil is substantially normal to a transverse axis of the wrap whereby magnetic flux is directionally generated perpendicularly with respect to a target area, further including a transverse substrate of metalized electromagnetic radiation shielding material adjacent to said outer surface of said applicator wrap said applicator wrap being adapted for placement contiguous to the injured body member for providing magnetic flux penetration within the selected target area.

2. A magnetotherapy apparatus as claimed in claim 1 further including an electrostimulation component having at least two stimulator pads, said stimulator pads being adapted for placement on the surface of a patient's skin, further including a low frequency pulsed d.c. current means said pads further being selectively energized by said low frequency pulsed d.c. current means for providing muscle stimulation.

3. A magnetotherapy apparatus as claimed in claim 2 wherein the operating frequency for the electrostimulation component is between 20–90 hertz.

4. A magnetotherapy apparatus as claimed in claim 1 further including an electrophoretic pharmaceutical delivery system having at least two applicator pads adapted for placement on the surface of a patient's skin, a network of tubing connected to said pads for delivering a selected pharmaceutical medium to the applicator pads, said applicator pads being selectively energized by a pulsed d.c. current means for drug treatment therapy.

5. A magnetotherapy apparatus as claimed in claim 1 further including a portable power source, said power source including a pulse signal generator, said pulse signal generator being in conductive communication with the magnetic coils to provide a pulsed signal having a frequency between 10–100 hertz for electromagnetic field therapy.

6. A magnetotherapy apparatus as claimed in claim 4 wherein the pulsed signal for the electrophoretic delivery system has a frequency of between 20–90 hertz.

7. A magnetotherapy apparatus as claimed in claim 1 wherein the applicator wrap is formed of molded thermoplastic material.

8. A magnetotherapy apparatus for use in combination with a bracing means for mobilizing an injured body member, said apparatus comprises a flexible wrap adapted for placement adjacent to a target treatment area, plural coil means positioned within the wrap for generating alternate successive magnetic fields of opposite polarity, said magnetic fields being adapted for penetrating the target area, said wrap including stimulator pad means, said pad means being selectively energized for providing muscular electrostimulation, further including a fluid reservoir said pad means further being in communication, with said fluid reservoir for selectively providing ionization of the fluid medium for delivery to the target area.

9. A multifunctional magnetotherapy apparatus for use in treating an injured body member, said apparatus comprising a flexible applicator wrap adapted for placement contiguous to the injured body member and below an overlying cast, said wrap incorporating a plurality of magnetic coils adapted for generating magnetic fields of opposite polarity when energized, said magnetic fields providing magnetic flux penetration perpendicularly directed with respect to the injured body member, said apparatus further including at least two stimulator pads positioned between said applicator wrap and a surface of the body member, said stimulator pads being spaced apart and, said pads further being selectively energized with opposite electrical charges for providing electrostimulation to the injured body member, further including a fluid reservoir in communication with stimulator pads, said reservoir supplying a drug medium to the stimulator pads, said pads being electrically charged for ionization of the drug medium for delivery to the injured body member.

* * * * *